United States Patent [19]

Alexandrides

[11] Patent Number: 5,981,578
[45] Date of Patent: Nov. 9, 1999

[54] INCREASED SOLUBILIZATION AND STABLE COSMETIC PREPARATIONS OF ASCORBIC ACID

[76] Inventor: Ariadne Alexandrides, 13827 Shavano Downs, San Antonio, Tex. 78230

[21] Appl. No.: 08/929,838

[22] Filed: Sep. 15, 1997

[51] Int. Cl.⁶ .............................. A61K 31/34; A61K 7/06; A61K 7/00; A61K 9/00
[52] U.S. Cl. ......................... 514/474; 424/70.1; 424/400; 424/401
[58] Field of Search ..................................... 424/400, 401, 424/70.1; 514/474

[56] References Cited

U.S. PATENT DOCUMENTS

| | | | |
|---|---|---|---|
| 4,818,521 | 4/1989 | Tamabuchi | 424/62 |
| 4,983,382 | 1/1991 | Wilmott et al. | |
| 5,140,043 | 8/1992 | Darr et al. | |
| 5,308,621 | 5/1994 | Taylor et al. | |
| 5,360,824 | 11/1994 | Barker | |
| 5,384,115 | 1/1995 | Bissett et al. | 424/59 |
| 5,587,149 | 12/1996 | Punto et al. | 424/59 |
| 5,744,146 | 4/1998 | Peters et al. | 424/401 |

OTHER PUBLICATIONS

USP 23, p. 130, 1995 Ascorbic Acid Monograph.

*Primary Examiner*—Shelley A. Dodson
*Assistant Examiner*—Marina Lamm
*Attorney, Agent, or Firm*—Royston, Rayzor, Vickery, Novak & Druce, L.L.P.

[57] ABSTRACT

Increased solubilization of ascorbic acid in organic solvents results in the formulation of potent compositions and the complete stabilization of this vitamin. Compositions comprising ascorbic acid and solubility increasing agents, such as avocado oil and avocado oil unsaponifiables, in organic solvents, may be topically applied in order to impart considerable aesthetic improvements to the skin.

10 Claims, No Drawings

INCREASED SOLUBILIZATION AND STABLE COSMETIC PREPARATIONS OF ASCORBIC ACID

BACKGROUND—FIELD OF INVENTION

This invention relates to new agents that increase the solubility of ascorbic acid (Vitamin C), and stable cosmetic compositions incorporating ascorbic acid in an non-aqueous base, which maintains it completely stable. This nonaqueous composition, when mixed with a face cream or lotion prepared with standard processes, is easily emulsified, and it imparts all of the known beneficial effects of Vitamin C on the skin.

BACKGROUND—DISCUSSION OF PRIOR ART

Ascorbic acid is essential to the maintenance of a healthy human skin. It delivers elasticity, short and long term firming action, reducing the adverse effects of the environment and the ageing of the skin. Ascorbic acid is an important factor in the regulation of the production of collagen in skin tissue, effecting the retardation of wrinkle formation and enhancing younger skin appearance.

Collagen formation slows down with advancing age. High concentrations of ascorbic acid, in aqueous formulations, accelerate collagen production. Skin appearance improves considerably.

The solubility characteristics of ascorbic acid have prevented the development and commercialization of elegant, potent and effective cosmetic preparations such as moisturizing creams and lotions. Ascorbic acid is soluble in water. Aqueous solutions of ascorbic acid are sensitive to light, oxidizing agents such as oxygen, and degrade in a wide pH range. In aqueous acidic solutions, the vitamin breaks down to dehydroascorbic acid. In aqueous alkaline solutions, it breaks down to hydrogen peroxide and 1-threonate ion. In concentrations of 10% or more, it may undergo decomposition in which carbon dioxide is produced. In just a few days, ascorbic acid aqueous preparations develop colors, progressively, from light yellow to orange dark brown. Ascorbic acid also tends to react with aqueous cosmetic matrices. All these reactions make development and commercialization of potent ascorbic acid products difficult. Manufacturers of cosmetic products, recognizing the beneficial effects of ascorbic acid on the skin, have incorporated extremely low levels of ascorbic acid in their cosmetic products. These products are ineffective. Ascorbic acid is difficultly soluble in organic solvents. The highest solubility is exhibited in propylene glycol to the extent of 3% to 4%. Because of this limited solubility, potent commercial products are not available. Solutions of ascorbic acid in organic solvents show exceptional stability. Efforts to develop ascorbic acid products are recognized from the great number of patents that have been awarded. The patents cited below have been selected as illustrations of these efforts:

Stable cosmetic compositions containing ascorbic acid have been claimed by James M. Wilmott and Alexander P. Zasiden in U.S. Pat. No. 4,983,382.

Stable topical aqueous compositions containing high levels of ascorbic acid were reported by Douglas Darr and Sheldon R. Pinnell in U.S. Pat. No. 5,140,043.

The following two patents report the use of solid powder particles of ascorbic acid suspended in an non-aqueous carrier:

Reginald M. Taylor and David J. Wilson, U.S. Pat. No. 5,308,621.

Donald E. Barker, U.S. Pat. No. 5,314,824.

OBJECTS AND ADVANTAGES

It is an object of the present invention to provide new ingredients that considerably increase the solubility of ascorbic acid in organic solvents, especially in propylene glycol.

It is another object of the present invention to provide a combination of two topically applied elegant creams, one containing ascorbic acid, in a non-aqueous matrix, and the second being a moisturizing cream.

Yet, another object of the present invention is to provide nonaqueous compositions containing ascorbic acid at levels equivalent to those achieved in aqueous compositions.

A further object of the present invention is to provide a non-aqueous cream containing ascorbic acid, devoid of coloration reactions that occur in aqueous systems containing it.

Yet a further object of the present invention is to provide a cream, lotion or gel containing ascorbic acid, of exceptional stability.

Another object of the present invention is to provide a combination of two topically applied creams that considerably improve the aesthetic appearance of the skin and simultaneously deliver the moisturizing effects of a face cream.

Yet another object of the present invention is to provide combinations of topically applied after shave lotions that eliminate or reduce irritation and improve the aesthetic appearance of the skin.

It is yet another object of the present invention to provide a readily emulsifiable gel containing ascorbic acid that will effectively cleanse the scalp, condition and repair damaged hair, when used in conjunction with a shampoo.

It is still another object of the present invention to provide a readily emulsifiable gel containing ascorbic acid that will impart an aesthetic appearance on the skin, with continued use and in conjunction with soap formulations.

In brief, this invention generally provides a topically applied combination of two products which include an active ingredient and cosmetically acceptable vehicles. The active ingredient is ascorbic acid, or a derivative thereof, stabilized and effective in reducing wrinkles, rejuvenating the skin, minimizing irritation, and minimizing the use of make up.

Still further, this invention provides a method for reducing wrinkles, irritation, and skin rejuvenation, which comprises the topical applications of an active ingredient, ascorbic acid or a derivative thereof, at a level that renders it very effective.

DETAILED DESCRIPTION OF SPECIFIC EMBODIMENTS

The problems of aqueous ascorbic acid solutions have been considered carefully and it has been concluded that, in a composition containing ascorbic acid, the absence of water is mandatory. It has also been recognized that an aqueous environment is required for the effective action of high levels of ascorbic acid, an action that may result in the retardation of the ageing process. This environment is provided by a separate product such as a moisturizing face cream or lotion. In conclusion, two different products, one nonaqueous containing the ascorbic acid, and a second providing water, should be applied simultaneously or sequentially on the skin.

The cosmetic difficulty of the low solubility of ascorbic acid in organic solvents such as propylene glycol, has been resolved by incorporating materials that increase the solubility of ascorbic acid in organic solvents. Non-aqueous ascorbic acid cream compositions, of exceptional stability, have been developed. These compositions, when mixed with a moisturizing cream, provide a superior moisturizing and revitalizing action on the skin. The mixing of the two cream compositions is performed on small quantities. The mixed products perform as a high quality face cream, creating such a rich aesthetic appearance on the skin that the need for make up is minimized. The two separate products of the non-aqueous cream composition and the moisturizing cream composition meet the desirable requirements of stability, discoloration, effectiveness and cosmetic elegance.

This invention contemplates the use of ascorbic acid and/or its derivatives. Derivatives of ascorbic acid include its cosmetically acceptable salts, esters and anhydrides. Examples of salts include alkali salts such as sodium ascorbate or potassium ascorbate, alkaline earth salts such as calcium ascorbate and magnesium ascorbate and mixtures thereof; esters include ascorbyl myristate, ascorbyl stearate, ascorbyl palmitate, ascorbyl laureate and mixtures thereof. Other salts include magnesium ascorbyl phosphate. The effective amounts of ascorbic acid and/or its derivative(s) will be at least about 1.0%, more preferably about 10% or most preferably about 15% and not more than 30%.

The vehicles that may be used in the nonaqueous creams, nonaqueous lotions, nonaqueous shampoos and nonaqueous gels, consist of an organic solvent, surfactants that function as emulsifying and solubilizing agents, skin conditioning agents, emollients, humectants, demulcents, moisturizers, colorants, preservatives, fragrances, viscosity modifying agents, and compatible mixtures thereof Examples of these vehicles include polyethylene glycol, glycerin, propylene glycol and mixtures thereof as the diluent; avocado oil unsaponifiables or avocado oil, as the solubility increasing agents, in the presence of emulsifying agents such as ceteareth or steareth. The other ingredients cited above may be used to improve the elegance of the cosmetic preparation. The cosmetic compositions are prepared using techniques very well known in the cosmetic arts.

The cosmetic compositions of this invention provide an exceptionally stable environment for ascorbic acid. The stability data demonstrate a product of unsurpassed stability with respect to ascorbic acid. When these compositions are applied topically to the skin, they impart a considerably improved appearance on the skin.

Solubility studies indicate that the highest solubility of ascorbic acid is in propylene glycol (3.5%). This solubility increases about five to six-fold in the presence of avocado oil unsaponifiables admixed with emulsifiers such as polyethylene glycol ether of cetearyl alcohol or polyethylene glycol ether of stearyl alcohol. The solubilization of ascorbic acid also increases by incorporating avocado oil in the presence of emulsifiers. Solutions of 10% ascorbic acid, 20% and even higher, in propylene glycol in the presence of solubility increasing agents, such as avocado oil unsaponifiables, avocado oil, and emulsifiers, are possible. Percentages are on a weight to weight basis. This discovery has led to the development of potent and stabilized cosmetic compositions of ascorbic acid, as the incorporation of water in these compositions is completely eliminated. Long term stability studies in ambient conditions have been conducted which demonstrate the stability of ascorbic acid in the solvent system described above. The ingredients in the listed compositions were dissolved by application of heat at 85 deg. C. to 95 deg. C. with continuous mixing. Heating continued until clear solutions were obtained. Upon cooling, readily emulsifiable creams were obtained. The products were packaged in a container/closure system consisting of a polypropylene bottle and a polypropylene closure. The products were stored under ambient conditions. Testing involved the assay of ascorbic acid, evidence of discoloration, and evidence of other reactions such as separation, gas formation, and liquifaction. Testing was conducted quarterly. The assay method was the USP 23 iodimetric for Ascorbic Acid. This method was validated before use. The stability data obtained below are expressed as percent of the expected level of ascorbic acid. The formulations placed in the stability program were A, B, and C as follows:

|  | Weight | | |
| --- | --- | --- | --- |
| Ingredient | A | B | C |
| Ascorbic Acid | 20.0 | 15.0 | 10.0 |
| Propylene Glycol | 35.0 | 35.0 | 35.0 |
| Cetearyl Alcohol (and) Ceteareth-20 | 10.0 | 10.0 | 10.0 |
| Avocado Oil | 19.7 | 24.7 | 29.7 |
| Glycerol | 8.0 | 8.0 | 8.0 |
| PPG-2 Myristyl Ether Propionate | 6.0 | 6.0 | 6.0 |
| Cyclomethicone | 1.3 | 1.3 | 1.3 |
| Totals | 100.0 | 100.0 | 100.0 |

The stability results obtained at the specified times, in months, are as follows:

| Months elapsed | 0 | 3 | 6 | 9 | 12 | 18 |
| --- | --- | --- | --- | --- | --- | --- |
| Formulation A | 20.3 | 20.2 | 20.2 | 20.1 | 20.1 | 20.1 |
| Formulation B | 15.0 | 15.0 | 14.9 | 14.9 | 14.8 | 14.8 |
| Formulation C | 9.99 | 9.97 | 9.92 | 9.89 | 9.88 | 9.88 |

These stability profiles render the marketability of products containing ascorbic acid feasible. All three formulations did not exhibit any discoloration during the entire stability program. No evidence of separation, gas formation or liquifaction occured.

This invention will now be further illustrated by means of specific examples which are not construed as limiting.

EXAMPLE 1

The following preferred composition was formed by mixing the ingredients at elevated temperatures. The product that forms is a readily emulsifiable face cream. Adjustment of the level of cetearyl alcohol (and) ceteareth yields a hand or after shave lotion.

| Ingredient | Weight |
| --- | --- |
| Ascorbic Acid | 15.0 |
| Propylene Glycol | 40.0 |
| Cetearyl Alcohol (and) Ceteareth-20 | 9.0 |
| Avocado Oil | 14.5 |
| Glycerin | 8.0 |
| PPG-2 Myristyl Ether Propionate | 6.0 |
| Cyclomethicone | 1.3 |
| Silicone Dioxide | 0.5 |
| Sodium Lauryl Sulfate | 0.5 |
| Fragrance | 0.2 |
| TOTAL | 100.0 |

This formulation is readily emulsifiable, and cosmetically very elegant.

EXAMPLE 2

| Ingredient | Weight |
| --- | --- |
| Ascorbic Acid | 5.0 |
| Avocado Oil | 4.0 |
| Hydroxyethylcellulose | 0.7 |
| Glycerin | 55.0 |
| Propylene Glycol | 30.3 |
| Avocado Oil Unsaponifiables | 5.0 |
| TOTAL | 100.0 |

In EXAMPLE 2, the hydroxyethylcellulose is allowed to gel in part of the glycerin at elevated temperature, and allowed to cool to about 80 deg C.; ascorbic acid is dissolved in the mixture of glycerin, propylene glycol, avocado oil unsaponifiables, and avocado oil by application of heat to about 90 deg. C. The two warm mixtures are mixed and thoroughly blended and the resultant gel is allowed to cool. If desired, the appropriate emulsifying agent may be added and incorporated in this formula. This product may be used as a gel, in conjunction with a hair shampoo to condition and repair damaged hair, and as an adjunct to shower soap.

In conclusion, this invention provides for a new solvent system effecting considerably an increased solubility of ascorbic acid resulting in compositions of long term stability, cosmetical elegance, and flexibility of ingredient use. The aesthetic benefits of the skin that the user experiences are considerable improvements in firmness, reduction of fine lines, wrinkles and pore size. In everyday use, the compositions of the present invention may be applied topically. After application, a standard moisturizing cream is applied to the same skin areas in order to create the optimum aqueous environment for the complete activation of ascorbic acid. In the case of lotion or gel formulations, wet skin areas are adequate to activate the ascorbic acid incorporated in the nonaqueous composition of this invention.

What is claimed:

1. A method for preparing a nonaqueous composition formulated for enhanced solubility and stability of ascorbic acid therein, said method comprising:

admixing to a nonaqueous organic solvent base an ascorbic acid solubility increasing agent having a capacity for increasing the proportionate amount of ascorbic acid solubilizable in said nonaqueous organic solvent base;

admixing thereto ascorbic acid, said ascorbic acid being stably solubilized within said nonaqueous composition in proportionate amounts at least as great as three times a maximum amount capable of being stably solubilized in said nonaqueous organic solvent base without said ascorbic acid solubility increasing agent; and thereby establishing a nonaqueous composition having enhanced solubility and stability of said ascorbic acid therein, said nonaqueous composition being anhydrous.

2. The method as recited in claim 1; wherein said proportionate amount of said ascorbic acid being stably solubilized within said nonaqueous composition is at least as great as six times the maximum amount of ascorbic acid capable of being stably solubilized in said nonaqueous organic solvent base without said ascorbic acid solubility increasing agent.

3. A method for improving the condition of skin, said method comprising:

applying a conditioning preparation to a subject's wet skin, said preparation including a nonaqueous composition comprising:

a nonaqueous organic solvent base having a capacity for accepting admixtures of ascorbic acid and an ascorbic acid solubility increasing agent;

an ascorbic acid solubility increasing agent having a capacity for increasing the proportionate amount of ascorbic acid solubilizable in said nonaqueous organic solvent base; and ascorbic acid stably entrained in said nonaqueous organic solvent base so that a resulting nonaqueous composition is anhydrous.

4. A method for improving the condition of skin, said method comprising:

applying a conditioning preparation to a subject's skin, said preparation including a nonaqueous composition comprising:

a nonaqueous organic solvent base having a capacity for accepting admixtures of ascorbic acid and an ascorbic acid solubility increasing agent;

an ascorbic acid solubility increasing agent having a capacity for increasing the proportionate amount of ascorbic acid solubilizable in said nonaqueous organic solvent base; and ascorbic acid stably entrained in said nonaqueous organic solvent base so that a resulting nonaqueous composition is anhydrous; and applying a moisturizer to the subject's skin thereby providing hydrating moisture to said conditioning preparation.

5. The method as recited in claim 4; further comprising:

activating said ascorbic acid by combining said moisturizer and said conditioning preparation topically on the subject's skin.

6. A method for preparing a conditioning shampoo, said method comprising:

admixing to a nonaqueous shampoo a nonaqueous composition, said nonaqueous composition comprising:

a nonaqueous organic solvent base having a capacity for accepting admixtures of ascorbic acid and an ascorbic acid solubility increasing agent;

an ascorbic acid solubility increasing agent having a capacity for increasing the proportionate amount of ascorbic acid solubilizable in said nonaqueous organic solvent base; and ascorbic acid stably entrained in said nonaqueous organic solvent base so that a resulting nonaqueous composition is anhydrous.

7. The method as recited in claim 1; wherein said nonaqueous organic solvent base is propylene glycol.

8. The method as recited in claim 1; wherein said ascorbic acid solubility increasing agent is an avocado oil unsaponifiable.

9. The method as recited in claim 1; wherein said ascorbic acid solubility increasing agent is avocado oil.

10. The method as recited in claim 1; wherein said nonaqueous organic solvent base is glycerin.

* * * * *